United States Patent [19]

Sosa et al.

[11] Patent Number: 5,731,173
[45] Date of Patent: Mar. 24, 1998

[54] FRUCTOSYLTRANSFERASE ENZYME, METHOD FOR ITS PRODUCTION AND DNA ENCODING THE ENZYME

[75] Inventors: Juan Gabriel Arrieta Sosa; Lazaro Hernandez Garcia; Alberto Coego Gonzalez; Guillermo Selman-Housein Sosa, all of Havana, Cuba

[73] Assignee: Center For Genetic Engineering and Biotechnology, Havana, Cuba

[21] Appl. No.: 814,196

[22] Filed: Mar. 10, 1997

Related U.S. Application Data

[62] Division of Ser. No. 362,232, Dec. 22, 1994, Pat. No. 5,641,667.

[30] Foreign Application Priority Data

Dec. 23, 1993 [CU] Cuba ............................................. 125/93

[51] Int. Cl.$^6$ .............................. C12P 19/18; C12N 9/10; C12N 1/00
[52] U.S. Cl. ............................... 435/97; 435/193; 435/823
[58] Field of Search ..................................... 435/193, 823, 435/97

[56] References Cited

PUBLICATIONS

Steinmetz, M. et al., "The DNA Sequence of the Gene for the Secreted *Bacillus Subtilis* Enzyme Levansucrase and its Genetic Control Sites," *Mol Gen Genet*, 200, 220–228 (1985).

Shimotsu, H. et al., "Modulation *Bacillus Subtilis* Levansucrase Gene Expression by Sucrose and Regulation of the Steady–State mRNA Level by sacU and sacQ Genes," *Journal of Bacteriology*, 168, 380–388 (1986).

Tang, L. et al., "Isolation and Characterization of Levansucrase–Encoding Gene from *Bacillus Amyloliquefaciens*," *Gene*, 96, 89–93 (1990).

Song, K. et al., "Nucleotide Sequence of Levansucrase Gene (levU) of *Zymomonas Mobilis* ZM1 (ATCC10988)," *Biochimica et Biophysica Acta*, 1173, 320–324 (1993).

Hernandez, L. et al., "Isolation and Enzymic Properties of Levansucrase Secreted by *Acetobacter Diazotrophicus* SRT4, a Bacterium Associated with Sugar Cane," *Biochemical Journal*, 309, 113–118 (1995).

Kyono, K. et al., "Cloning and Characterization of *Zymomonas Mobilis* Genes Encoding Extracellular Levansucrase and Invertase," *Biosci. Biotech. Biochem.*, 59 (2), 289–293 (1995).

Arrieta, J. et al., "Molecular Characterization of the Levansucrase Gene From the Endophytic Sugarcane Bacterium *Acetobacter Diazotrophicus* SRT4," *Microbiology*, 142, 1077–1085 (1996).

*Primary Examiner*—Robert A. Wax
*Assistant Examiner*—Lisa J. Hobbs
*Attorney, Agent, or Firm*—Hoffmann & Baron, LLP

[57] ABSTRACT

Extracellular fructosyltransferase of *Acetobacter diazotrophicus* was isolated and purified and its enzymatic properties were established. Cloning, sequencing and genetic manipulation of the fructosyltransferase gene so as to produce high levels of the enzyme in recombinant prokaryotic and eukaryotic cells. Both natural and recombinant fructosyltransferase of *Acetobacter diazotrophicus* produce fructose-containing oligosaccharides and fructans. The enzyme yields in particular high levels of fructooligosaccharides from sucrose, such as kestose and kestotetraose which can be used as natural low-calorie sweeteners.

6 Claims, No Drawings

FRUCTOSYLTRANSFERASE ENZYME, METHOD FOR ITS PRODUCTION AND DNA ENCODING THE ENZYME

This application is a division of U.S. Ser. No. 08/362,232 filed on Dec. 22, 1994 now U.S. Pat. No. 5,644,667.

FIELD OF THE INVENTION

The present invention is in the field of biotechnology and is specifically concerned with the isolation, the purification, the characterization and the production of a fructosyltransferase. The invention also relates to the cloning, the sequencing and the manipulation of a fructosyltransferase gene so as to allow the production of high levels of recombinant enzyme.

BACKGROUND OF THE INVENTION

Production and utilization of microbial fructans by enzymatic transformation of sucrose are an important object for the sugar, food, and other industries. Bacterial fructosyltransferases (EC 2.4.1.10) catalyze the synthesis of oligo- and/or polyfructans by transferring fructosyl moieties from sucrose-containing saccharides to acceptor molecules. Different compounds can be used as acceptors which allows the enzymatic production of nondigestible homo- and heterooligosaccharides with beneficial effects on humans and animals.

Most of the bacterial fructosyltransferases characterized so far are levansucrases (Cote, G. L. and Ahlgran, J. A., In Science and Technology of fructans. Metabolism in microorganisms, Part I: Levan and levansucrase. CRC Press, 1993). All levansucrases catalyze the transfructosylation reaction from sucrose to a variety of acceptors such as water (sucrose hydrolysis), glucose (exchange reaction), fructose (chain elongation) and sucrose (synthesis of oligosaccharides). However, differences have been noted between these enzymes pertaining to the relative efficiency of each reaction which leads to the accumulation of oligofructans of different polymerization degree.

Several bacteria and fungi have been identified to develop transfructosylation reactions from sucrose (for review see Cote, G. L. and Ahlgran, J. A., In Science and Technology of fructans. Metabolism in microorganisms, Part I: Levan and levansucrase. CRC Press, 1993). Fructosyltransferase genes have been isolated from *Bacillus subtilis* (European patent application EP 0117823 A1 840905), *Bacillus amyloliquefaciens* (Tang, L. B. et al., Gene 96, 89–93, 1990), *Streptococcus mutans* (Shiroza, T. et al., J. Bacteriol. 170, No. 2, 810–816, 1988), *Streptococcus salivarius* (Rathsam, C. et al., J. Bacteriol. 175, No. 14, 4520–4527, 1993), *Zymomonas mobilis* (Ki-Bang Song et al., Biochim. Biophys. Acta 1173, 320–324, 1993) and *Erwinia amylovora* (Geier, G. et al., Physiological and Molecular Plant Pathology 42, 387–404, 1993). Low homology is found among the deduced amino acid sequences of fructosyltransferases isolated from different bacterial genera.

The transfructosylation system of the genus Bacillus (Gram-positive bacteria) has been well characterized. The *Bacillus subtilis* levansucrase is an inducible exoenzyme which catalyzes the formation of high weight polymer without accumulation of transient oligofructans of low polymerization degree. Recombinant levansucrases of *Bacillus subtilis* have been obtained in genetically manipulated hosts such as bacteria (Philippe, G. J. Bacteriol. 153, No. 3, 1424–1431, 1983), yeast (Scotti, P. A. et al., Yeast 10, No. 1, 29–38, 1994) and planes (Ebskamp, M. J. M. et al., Biotechnology 12, 272–275, 1994).

*Acetobacter diazotrophicus* is the most recently identified species of the genus Acetobacter (Gillis et al., Int. J. Sist. Bacteriol. 39, 361–364, 1989). The cells are Gram-negative, $N_2$-fixing, acid-tolerant, microaerobic, straight rods with rounded ends, about 0.7 to 0.9 by ±2 µm, motile by lateral or peritrichous flagella. The bacteria are non-pathogenic and further distinguished by their ability to establish beneficial association with sugarcane. However, the molecular biology of the bacterium has been poorly investigated.

SUMMARY OF THE INVENTION

*Acetobacter diazotrophicus* secretes a constitutive fructosyltransferase with levansucrase activity. The enzyme has utility for the production of fructose-containing oligosaccharides and levan. Fructose polymers have two characteristic properties, their nondigestibility and selective utilization by beneficial intestinal bacteria, which make them useful as low-calorie dietary fiber for relief of constipation, improvement of blood lipid composition, cholesterol reduction, and suppression of intestinal putrefactive substances. During the course of sucrose transformation the *Acetobacter diazotrophicus* fructosyltransferase accumulates a high yield of fructooligosaccharides, particularly kestose and kestotetraose which can serve as natural low-calorie sweeteners. Levan can also be used as a source of fructose, a blood plasma volume extender, an emulsifier, an encapsulating agent, etc.

Given the importance of fructooligosaccharides and levan as foodstuffs as well as their industrial applications, it is an object of the invention to produce the fructosyltransferase of *Acetobacter diazotrophicus* both by natural and by recombinant procedures.

The invention provides a method for isolating, characterizing and producing an *Acetobacter diazotrophicus* fructosyltransferase by natural and recombinant procedures.

The fructosyltransferase of *Acetobacter diazotrophicus* is a constitutive exoenzyme which is accumulated in the culture medium yielding more than 70% of total secreted proteins. The culture supernatant can be used as a crude fructosyltransferase solution, or the enzyme be purified by any conventional method applicable here, preferably ion-exchange chromatography.

The fructosyltransferase of *Acetobacter diazotrophicus* is a levansucrase which yields a high level of oligofructans of low polymerization degree. During the course of sucrose transformation 55% of fructose transferred by the enzyme is accumulated as kestotriose and kestotretraose. These fructooligosaccharides are high quality sweeteners with many applications in the food industry. The enzyme can be efficiently applied, therefore, for producing kestose and kestotetraose from sucrose, and it is also useful in the production of high weight levan.

The invention also comprises the nucleotide sequence of the fructosyltransferase gene of *Acetobacter diazotrophicus* isolated from a genomic library by complementing EMS-treated mutants of *A. diazotrophicus* unable to produce levan.

The production of the fructosyltransferase of *A. diazotrophicus* by recombinant procedures allows higher levels of enzyme production as well as the synthesis of the enzymatic reaction products directly in a convenient host. Also provided for are strains from *E. coli* and the yeast *Pichia pastoris* genetically manipulated so as to produce elevated levels of the recombinant fructosyltransferase.

DETAILED DESCRIPTION OF THE INVENTION

As used herein, the term "Acetobacter" refers to a particular genus of bacteria described in detail in Bergey's Manual of Determinative Bacteriology, Buchanan and Gibbons eds., Williams and Wilkins Publishers. The specific strain of Acetobacter from which the enzyme fructosyltransferase and the corresponding gene were isolated is *Acetobacter diazotrophicus* SRT4 (CBS deposit number CBS 549.94, deposition date 10 Nov., 1994).

For the purpose of the present invention the term "fructosyltransferase" refers to one or more polypeptides having fructosyltransferase activity. Fructosyltransferase activity refers to the property of enzymatically transferring fructosyl moieties from sucrose-containing saccharides to acceptor molecules to yield fructooligosaccharides and fructans.

The term "recombinant protein" as used herein intends to cover a polypeptide encoded by genomic, cDNA, semisynthetic or synthetic nucleic acid sequences which, by virtue of their origin or manipulation: (1) are not associated with all or a portion of the polynucleotide with which they are associated in nature or in the form of a library; and/or (2) are linked to a polynucleotide sequence other than that to which they are linked in nature. The recombinant protein displays substantially the same biological properties as the naturally occurring protein.

In a first aspect, the present invention provides an isolated and purified DNA having a nucleotide sequence which essentially corresponds to or hybridizes with a nucleotide sequence comprised in the fructosyltransferase gene, shown in Seq. Id. No.1, of the bacterium *Acetobacter diazotrophicus*.

The words "a nucleotide sequence comprised in the fructosyltransferase gene" are intended to include several possibilities. One option is a DNA which covers the complete fructosyltransferase gene, i.e. the gene inclusive of regulatory and coding sequences. Another option is a DNA essentially consisting of the coding sequence, or a part of the coding sequence, and lacking the fructosyltransferase promoter region. One such possibility is a fructosyltransferase cDNA obtained by reverse transcription from fructosyltransferase mRNA. Furthermore, the invention relates to oligonucleotides of sufficient length to be specific for fructosyltransferase DNA or RNA. Such oligonucleotides may be useful as fructosyltransferase-specific probes or primers and will usually have a length of from about 7 or 8, preferably from about 9 or 10 nucleotides up to about 40 or 50 nucleotides, preferably to about 25 or 30 nucleotides, or longer, up to the full length of the gene.

The words "a nucleotide sequence which essentially corresponds to or hybridizes with" are intended to include single stranded and double stranded DNA. In the case of single stranded DNA, both the corresponding and the complementary sequence are intended to be included by this wording.

The correspondence need not be 100%, i.e. DNA having a certain homology to the sequence shown in Seq. Id. No.1 is intended to be included. DNA which has a homology of at least 60%, preferably a homology of at least 70% to said sequence is intended to be covered. It is especially intended to cover DNA having the same function and/or effect, even though the sequence differs from the one shown in Seq. Id. No.1. Thus, the invention is intended to include any changes in the fructosyltransferase coding region which either lead to the same amino acid sequence or to an amino acid sequence which, notwithstanding one or more deviations from the original amino acid sequence, corresponds to an enzyme having essentially fructosyltransferase activity.

For example, the invention intends to cover not only the genomic DNA and cDNA which codes for the fructosyltransferase enzyme of an *Acetobacter diazotrophicus*, but also DNA coding for related fructosyltransferase enzymes, e.g. DNA coding for the fructosyltransferase enzyme of related bacteria. Fructosyltransferase enzymes are considered to be related when they have a similar fructosyltransferase activity, and/or are recognized by the same antifructosyltransferase antibody, and/or are encoded by DNA having a homology of at least 60 or 70%.

According to a preferred embodiment of the invention, the DNA comprises a nucleotide sequence coding for an enzyme having fructosyltransferase activity. More preferably, said nucleotide sequence codes for an *Acetobacter diazotrophicus* fructosyltransferase enzyme having the amino acid sequence shown in Seq. Id. No.2. More specifically, said nucleotide sequence essentially consists of the nucleotide sequence shown in Seq. Id. No.1.

A further aspect of the present invention provides a recombinant polynucleotide comprising a DNA as defined above (a fructosyltransferase-specific DNA) and a nucleotide sequence of a cloning or expression vector, wherein said polynucleotide is able to direct the expression of a protein in a suitable host, more in particular a protein with fructosyltransferase activity. Said host may be a bacterium, such as a strain of *E. coli*, in which case the plasmid pUCLS28 is a good example of a suitable recombinant polynucleotide. The host may also be a yeast, such as the yeast *Pichia pastoris*, in which case the plasmid pPSLS20 is a good example of a suitable recombinant polynucleotide. The invention is not limited to particular kinds of hosts, however. In principle, any prokaryotic or eukaryotic cell may be used.

A further aspect of this invention is a host cell transformed with a recombinant polynucleotide as defined above. As indicated above, the host cell may for example be a bacterium, such as a strain of *E. coli*, e.g. the strain Lev1 of *E. coli*, or a yeast, such as the yeast *Pichia pastoris*, e.g. the strain Lev2 of *Pichia pastoris*.

An important further aspect of this invention is a proteinaceous substance having fructosyltransferase activity which comprises a polypeptide having an amino acid sequence essentially as shown in Seq. Id. No.2, or a fragment of the same. In a particularly preferred embodiment of the present invention, the proteinaceous substance having fructosyltransferase activity has a molecular weight of about 60000 daltons and an isoelectric point of about 5.5, is stable in a pH range between 4 and 9 and in a temperature range between 10° and 70° C., is active in the presence of 2% SDS, has an activity recovered after 5M urea treatments, has a specific activity of 2600 U/mg, has a Km for sucrose hydrolysis at 30° C. and pH 5.8 of about 12 mM, is not able to transfer fructosyl moieties to inulin and has a low levanase activity.

The invention covers the enzyme irrespective of how it has been produced, for example by recombinant DNA/ genetic engineering technology, chemical synthesis, enzymatic degradation, or a combination thereof. Further, the invention not only covers the enzyme as such, but also in the form of a fusion protein or as a protein physically or chemically bound to any substance and having fructosyltransferase activity.

Another aspect of this invention is a method for producing a proteinaceous substance having fructosyltransferase activity, comprising the expression in a suitable host of a DNA as defined herein which codes for a fructosyltransferase enzyme. As stated above, the expression may be in prokaryotic or eukaryotic cells. This invention includes a method as defined above wherein the fructosyltransferase enzyme produced is recovered from the cells and/or the culture medium.

The invention furthermore provides a method for producing a proteinaceous substance having fructosyltransferase activity, comprising culturing a strain of *Acetobacter diazotrophicus* and recovering the fructosyltransferase enzyme produced. Preferably the *Acetobacter diazotrophicus* strain SRT4 (CBS 543.94) is used. Again the fructosyltransferase enzyme produced may be recovered, preferably from the culture medium. Recovery may be in the form of the culture medium as such, or by isolation and purification of the enzyme from the culture medium.

The isolated fructosyltransferase is characterized by the following enzymatic properties.

(1) The enzyme acts at least on sucrose and raffinose to transfer the fructosyl group to a broad range of acceptor (or receptor) molecules.

(2) The enzyme hardly exhibits activity on kestose and nistose.

(3) The enzyme shows low levanase activity and does not transfer fructosyl moieties to inulin.

(4) The enzyme has optimal activity at pH 5 and is stable in the range from 4 to 9.

(5) The enzyme is active in a temperature range from 10° to 70° C.

(6) The enzyme activity is not affected in the presence of 2% SDS.

(7) The enzyme consists of a single polypeptide of 60000 daltons as estimated by SDS-polyacrylamide gel electrophoresis.

(8) The isoelectric point of the enzyme is 5.5.

(9) The enzyme is susceptible to the inhibitive effect of the ions of mercury.

(10) The Km value for sucrose hydrolysis at 30° C. and pH 5.8 is 11.8 mM.

(11) The specific activity of the enzyme is 2600 U/mg. One unit of enzyme is defined as the amount of enzyme releasing 1 µmole of glucose per minute at 42° C. and pH 5.2.

The fructosyltransferase used in the inventive method can be naturally produced by inoculating a suitable culture medium with the strain SRT4 of *Acetobacter diazotrophicus* and conducting culturing of the microorganism under shaking or aeration at a temperature of 20° C. to 40° C., preferably 30° C. and at a pH value of 5 to 6.5, preferable 5.5 for a length of time of 12 hours to 3 days. In the culture medium preferable carbon sources include glucose, fructose, sucrose, glycerol, sorbitol and mannitol. Generally satisfactory results can be obtained by using a culture medium containing 2% of mannitol, 0.1% of yeast extract, 0.1% of tryptone, 0.12% of $KH_2PO_4$, 0.04% of $K_2HPO_4$, 0.02% of $MgSO_4.7H_2O$, 0.002% of $CaCl_2.H_2O$, 0.001% of $FeCl_3$ and 0.0002% of $Na_2MoO_4$ having a pH of 6.0.

The naturally occurring fructosyltransferase of *Acetobacter diazotrophicus* is accumulated in the culture medium during the late phase of bacterial growth representing more than 70% of the total extracellular proteins. Since it is not inducible with sucrose, the enzyme can be obtained by culturing the microorganism in the presence of a preferable carbon source other than sucrose so that levan is not formed in the culture medium, which gives a great practical advantage in the recovery of the secreted enzyme.

After culturing, the cells are removed, preferably by centrifugation, and the supernatant can be used as a crude enzyme solution or if necessary the enzyme can be purified according to a conventional enzymological procedure, preferably ion-exchange chromatography.

The invention also provides the polynucleotide sequence coding for the fructosyltransferase of *Acetobacter diazotrophicus*. This DNA sequence reveals low homology wink known fructosyltransferase genes. Recombinant DNA molecules comprising the provided coding sequence can be constructed by genetic engineering techniques to express desired levels of the enzyme in a variety of host cells.

Of particular interest is the expression of fructosyltransferase in a recombinant host so as to synthesize the transfructosylation products directly in the said host. Cells of interest for fructosyltransferase expression may be eukaryotic or prokaryotic, being preferred eukaryotic cells such as yeast and plant cells. Of interest is also the construction of recombinant DNA molecules comprising a modified fructosyltransferase gene so as to modulate the catalytic properties of the recombinant enzyme.

The invention further provides recombinant DNA molecules so as to produce elevated levels of the recombinant fructosyltransferase in genetically manipulated cells of *E. coli* and the yeast *Pichia pastoris*. Increased levels of expression may be achieved by a variety of genetic manipulations, including placing the encoded gene on multicopy plasmids, and/or operably linking high level promoters and other transcriptional control sequences (operators, attenuators and the like). Thus the regulation of the fructosyltransferase gene may be altered so as to provide for inducible or constitutive expression in recombinant host cells.

The invention also provides a method for producing fructooligosaccharides and/or fructans by means of sucrose transfructosylation comprising contacting sucrose under suitable transfructosylation conditions with a fructosyltransferase enzyme or with cells producing a fructosyltransferase enzyme and optionally recovering the fructooligosaccharides produced, wherein said fructosyltransferase enzyme is a proteinaceous substance as defined herein or a proteinaceous substance obtained by a method as defined herein. Additionally, the fructosyltransferase enzyme or cells producing fructosyltransferase enzyme may be used in an immobilized form, physically or chemically coupled to a carrier material.

The fructosyltransferase of *Acetobacter diazotrophicus* can be used to transfer fructosyl residues to different acceptor compounds, which allows for example the synthesis of homo- and heterooligosaccharides or fructans, the hydrolysis of sucrose, etc. The enzyme can be used also to eliminate fructose from any substance that can function as donor of such residue. Using this enzyme it is possible to change the properties of an organism by changing its carbohydrate profile through the fructosyltransferase expression. As applications, for example, the products of the transfructosylation reaction can be obtained directly from said organism or alternatively the presence of said products, at low levels, could change the form of the crystals of a substance obtained from said organism, so as to facilitate its purification.

STRAIN DEPOSITS

An *Acetobacter diazotrophicus* strain SRT-4 was deposited on 10 Nov. 1994 with the Centraalbureau voor Schimmelcultures (CBS), The Netherlands, under the provisions of the Budapest Treaty and received accession number CBS 549.94.

An *E. coli* strain S17-1 containing p21R1 was deposited on 10 Nov. 1994 with the Centraalbureau voor Schimmel-

7 cultures (CBS), The Netherlands, under the provisions of the Budapest Treaty and received accession number CBS 550.94.

EXAMPLES

Examples are offered by way of illustration, not by way of limitation.

Example 1

Isolation of a levan-producing strain of *Acetobacter diazotrophicus*.

Stem segments (1 cm size) of sugarcane cultivar Ja60-5 were collected, superficially sterilized and inoculated into vials with 3 mL of semisolid LGI medium consisted of: $K_2HPO_4$ 0.02%, $KH_2PO_4$ 0.06%, $MgSO_4 \cdot 7H_2O$ 0.02%, $CaCl_2 \cdot 2H_2O$ 0.002%, $Na_2MoO_4 \cdot 2H_2O$ 0.0002%, $FeCl_3$ 0.001%, bromothymol blue 0.0025%, sucrose 10%, agar 0.18%, final pH 6.0. Semisolid LGI medium was reported for selective isolation of nitrogen-fixing bacteria of the species *Acetobacter diazotrophicus* (Cavalcante V. A. et al., Plant Soil 108: 23–31, 1988). Vials were incubated at 30° C. until growth was observed, such vials were replicated into semisolid LGI medium and those showing the typical orange-yellow surface growth were streaked out on LGI medium plates. Several mucous colonies were taxonomically characterized and classified as *Acetobacter diazotrophicus*, one of the isolates was named strain SRT4.

Example 2

Analysis of the extracellular polymer produced by *Acetobacter diazotrophicus* strain SRT4 grown on sucrose-containing media.

Bacteria were grown on solid LGI medium at 30° C. for 7 days. The extracellular polymer synthesized was collected from the medium surface with distilled water. After bacteria were removed by centrifugation, the polymer was precipitated with 2 volumes of ethanol, redissolved in distilled water, treated with saturated phenol, twice precipitated with ethanol, dialyzed against distilled water and freeze-dried. The molecular weight of the purified polymer was $7 \times 10^6$ daltons, as estimated by gel filtration on a Sephacryl S-500 column (20×0.8 cm) eluted with 0.2M NaCl at a flow rate of 12 ml $h^{-1}$. Total acid hydrolysis of purified polymer was performed with 0.5M $H_2SO_4$ at 100° C. for 15 min and neutralized with $Ba(OH)_2$. After total hydrolysis, the polymer composition was found to be fructose, as analyzed by HPLC using a Nucleosil $NH_2$ column (25×0.8 cm) eluted with 80% acetonitrile in water at a flow rate of 0.4 ml $min^{-1}$ in an isocratic way. Polymer analysis by $^{13}C$-NMR spectroscopy revealed the presence of β-D-(2,6)-linked fructofuranosyl residues in a greater extent and a low rate of β-D (2-1)-linkages. This polymer structure is consistent with bacterial levans.

Example 3

Production of the exoenzyme fructosyltransferase of *Acetobacter diazotrophicus*.

The fructosyltransferase of *Acetobacter diazotrophicus* is a constitutive exoenzyme which is accumulated in the culture medium during the late phase of growth yielding more than 70% of total extracellular proteins.

The *Acetobacter diazotrophicus* strain SRT4 was grown in a 5 L fermenter (3.5 L working volume) B. E Marubishi (Tokyo, Japan) to stationary phase in a medium consisting of: mannitol 2%, yeast extract 0.1%, tryptone 0.1%, $KH_2PO_4$ 0.12%, $K_2HPO_4$ 0.04%, $MgSO_4 \cdot 7H_2O$ 0.02%, $CaCl_2 \cdot H_2O$ 0.002%, $FeCl_3$ 0.001%, $Na_2MoO_4$ 0.0002%. The fermentation conditions were: temperature 30° C., pH 5.5, stirring speed 400 rpm, aeration 1 vvm (1 volume per minute). The culture reached a stationary $OD_{620}$ of 9.5 after fermentation for 60 hrs. The cells were removed by centrifugation and the culture supernatant was concentrated 5 fold using a rotatory evaporator and dialyzed against 20 mM Tris-HCl pH 7.0. Subsequently, ammonium sulfate was added to give 70% saturation. After centrifugation, the precipitate was dissolved in 20 mM Tris-HCl pH 7.0, dialyzed against the same buffer and applied to a column (2.5×13 cm) of DEAE-Sepharose CL-6B (fast flow). The proteins absorbed on the column were selectively eluted with a linear concentration gradient of NaCl in buffer 20 mM Tris-HCl pH 7.0. The fractions with fructosyltransferase activity eluted with the NaCl concentrations of 0.2 to 0.25M. The eluted fractions were pooled, dialyzed against a solution of 1% $NH_4HCO_3$ pH 8.0 and lyophilyzed. The purified enzyme was applied on SDS-PAGE showing a single band of approximately 60 000 daltons. The N-terminal sequence of the mature fructosyltransferase is Gly Gly Pro Leu Phe Pro Gly Arg Ser Leu (Seq. Id. No.3) as determined by the Edman degradation procedure.

The following table shows the fructosyltransferase activity, the protein content, the specific fructosyltransferase activity and the yield in the fructosyltransferase-active fractions obtained in the individual steps of the purification procedure described above.

| Purification step | Total activity (U) | Total protein (mg) | Specific activity (U/mg) | Recovery (%) | Purification (fold) |
| --- | --- | --- | --- | --- | --- |
| Culture supernatant (10 liters) | 449280 | 288 | 1560 | 100 | 1 |
| Ammonium sulfate (70% saturation) | 323880 | 169 | 1507 | 57 | 0.96 |
| DEAE-Sepharose CL-6B (fast flow) | 128991 | 49 | 2618 | 28 | 1.68 |

The isolated fructosyltransferase is characterized by the following enzymatic properties.

(1) The enzyme acts at least on sucrose and raffinose to transfer the fructosyl group to a broad range of receptor molecules.

(2) The enzyme hardly exhibits activity on kestose and nistose.

(3) The enzyme shows low levanase activity and does not transfer fructosyl moieties to inulin.

(4) The enzyme has optimal activity at pH 5 and is stable in the range from 4 to 9.

(5) The enzyme is active in a temperature range from 10° to 70° C.

(6) The enzyme activity is not affected by 2% SDS.

(7) The isoelectric point of the enzyme is 5.5.

(8) The enzyme is susceptible to the inhibitive effect of the ions of mercury.

(9) The Km value for sucrose hydrolysis at 30° C. and pH 5.8 is 11.8 mM.

(10) The specific activity of the enzyme is 2600 U/mg.

Example 4

Production of fructooligosaccharides by the action of the *A. diazotrophicus* fructosyltransferase on sucrose.

Levansucrase was added to a reaction mixture containing sucrose 1M in acetate buffer 0.1M, p.H 5.8, in a ratio of 30 units of enzyme per gram of sucrose. The reaction was conducted at 30° C. for 3 hours. Analysis of sugar products by paper chromatography on Whatman 3 MM paper in 4:6:3 pyridine: butan-1-ol:water revealed that 55% of total released fructose was accumulated in kestose in the reaction mixture. A further analysis of the reaction products was carried out by high performance liquid chromatography (HPLC) on Dionex carbopac TM PAL (column 4×250 mm) showed the following sugar composition: 31% glucose (G); 17% fructose (F); 23% sucrose; 18% kestose (GF2); 6% nistose (GF3); 3% fructosylnistose (GF4); 2% fructan (GF>4).

Example 5

Isolation of *Acetobacter diazotrophicus* mutants deficient in levan synthesis (Lev⁻ phenotype) by EMS mutagenesis.

Lev⁻ mutants were obtained by mutagenesis with ethyl-methanesulfonate (EMS) according to the method described by Miller (Miller, J. H. 1972, Experiments in Molecular Genetics. Cold Spring Harbor Laboratory, Cold Spring Harbor, N.Y.) with some modifications. The *A. diazotrophicus* strain SRT4 was grown aerobically in SB medium for 48 hours at 30° C. Bacteria (1.5 ml culture in an eppendorf tube) were harvested by centrifugation, washed in 1.5 ml of LGI medium salts, resuspended in 0.5 ml of 2% EMS in 0.2M Tris-HCl pH 7.4 and incubated for 90 minutes at 30° C. The treated cells were collected by centrifugation, washed with 1 ml of 5% $NaS_2O_3$ in 0.2M Tris-HCl pH7.4, resuspended in 3 mL of SB medium supplemented with glycerol 1% and grown with aeration for 16 hours at 30° C. The bacterial culture was plated onto LGIE medium (LGI medium salts, tryptone 0.1%, yeast extract 0.02%) with sucrose 5% and glycerol 1% and incubated at 30° C. Colonies showing a non-mucous phenotype were picked, grown in liquid LGIE medium and assayed for fructosyltransferase activity. Nine Lev⁻ mutants were obtained at a frequency of $2.5\times10^{-4}$. Two classes of mutants were isolated according to the phenotype: class I mutants did not show neither extracellular nor intracellular fructosyltransferase activity, probably due to mutations in the enzyme gene; class II mutants did not show fructosyltransferase activity in the culture supernatant but still maintain the intracellular activity.

Example 6

Construction of a genomic clone coding for the *A. diazotrophicus* fructosyltransferase.

Routine recombinant DNA procedures were performed by standard methods essentially as described in Maniatis 1989, Molecular Cloning, CSH, N.Y., USA.

A genomic library of *A. diazotrophicus* strain SRT4 was constructed in the broad-host-range cosmid pPW12, a derivative of pLAFR1 (Friedman et al., Gene 18, 289–296, 1982) with a synthetic sequence containing the EcoRI-BamHI-EcoRI sites inserted at the EcoRI site (AFRC-IPSR Nitrogen Fixation Laboratory, University of Sussex, Brighton, East Sussex, BN19KQ, United Kingdom).

Total DNA from *A. diazotrophicus* strain SRT4 was partially digested with the restriction endonuclease Sau3A I. Fragments of 15–30 kb were isolated from a low melting temperature agarose gel and cloned into BamHI-cleaved and dephosphorylated vector pPW12. The library was packaged into lambda phage particles, transferred by infection to *E. coli* strain S17-1 (Simon, R. et al., pp 98–106, en A. Puhler ed. Molecular Genetics of the bacteria-plant interaction, Springer-Verlag, Berlin) and plated onto LB medium supplemented with tetracycline 12 ∝g/ml. Then the gene bank was collected and transferred by conjugation to a Lev⁻ class I mutant strain isolated from the *Acetobacter diazotrophicus* strain SRT4.

For conjugal mating the Lev⁻ mutant strain of *A. diazotrophicus* was grown aerobically for 36 hours at 30° C. in SB medium with 1% glycerol as carbon source, 1.5 ml of bacterial culture were sedimented by centrifugation for 5 minutes at 12000 rpm and the cells resuspended in 0.3 mL of LGI medium salts. Simultaneously 1 ml of the gene library kept in glycerol was inoculated to 2 ml of LB medium and incubated with aeration at 37° C. for 3 hours. The cells were harvested by centrifugation and resuspended in 0.3 ml of M9 medium salts. The *A. diazotrophicus* mutant strain and the *E. coli* cells carrying the gene library were mixed on GYC agar plates (5% glucose, 1% yeast extract, 3% $CaCO_3$) (De Ley, J et al., pp 268–274, en N. R. Krieg & J. G. Holt ed Bergey's manual of Systematic Bacteriology, 8th ed. The Williams & Wilkins Co., Baltimore, 1984) and grown for 48 hours at 30° C. The mating mixture was collected and plated onto LGIE agar medium with 5% sucrose supplemented with ampicillin 25 μg/ml (included to select against *E. coli*) and tetracycline 20 μg/ml for transconjugant selection. Individual colonies which recovered the mucous phenotype were picked. Plasmidic DNA from these revertants was purified, used to transform the *E. coli* strain S17-1 and transferred back by conjugation to the *A. diazotrophicus* mutant strain ascertaining that the phenotypic complementation of the Lev⁻ mutant was due to the information carried on the plasmids.

As a result of restriction endonuclease mapping, two recombinant cosmids identified as p21R1 and p21R2 were found to share a common 7.8-kb region. By several subcloning and complementation experiments, the fructosyltransferase gene was located in a 2.3 kb BglII fragment. This fragment was cloned into pUC18 (C. Yanisch-Perron et al., 1985, Gene 33: 103–119) and named pUCLS23. Nucleotide sequencing of this region revealed the presence of an open reading frame which codes for a protein with certain homology to the fructosyltransferases published so far. A smaller 2.0 kb SmaI fragment from pUCLS23 containing only this open reading frame was ligated in-frame into the 5'-region of lacZ' of pUC18 vector (C. Yanisch-Perron et al., 1985, Gene 33: 103–119) under the control of the $P_{lac}$ promoter. The constructed plasmid named pUCLS20 was used to transform the *E. coli* strain 71-18 (C. Yanisch-Perron et al., 1985, Gene 33: 103–119). The resulting recombinant strain identified as Lev1 was grown in LB medium at 37° C. and the expression of the cloned gene was induced with isopropylthiogalactoside (IPTG). The polypeptide expressed in *E. coli* was detected in western blot by rabbit antibodies raised against the *A. diazotrophicus* fructosyltransferase. The recombinant protein exhibited the expected molecular mass (60 000 daltons) and showed fructosyltransferase activity as the natural enzyme.

These results demonstrate that the identified open reading frame in the recombinant plasmid pUCLS23 codes for the fructosyltransferase of *Acetobacter diazotrophicus*. The nucleotide sequence of the fructosyltransferase gene corresponds to the Seq. Id. No.1. The amino acid sequence deduced from the nucleotide sequence of said gene corresponds to the Seq. Id. No.2.

Example 7

Production of an enzymatic preparation with fructosyltransferase activity in recombinant E. coli.

The recombinant E. coli strain Lev1 was inoculated to an erlenmeyer containing 300 ml of LB medium supplemented with 0.5% glucose and grown in a rotatory shaker at 37° C. for 16 hours. This culture was used to inoculate a 5 L fermenter (working volume 3.5 L) B. E Marubishi (Tokyo, Japan) containing LB medium supplemented with 0.5% glucose at an initial $OD_{530}$ of 0.05. The fermentation conditions were as follows: 37° C., pH 6.8–7.2, stirring speed 350 rpm and aeration 1 VVM (1 volume per minute). When the $OD_{530}$ reached a value of 2 the culture was induced with 1 mM of isopropylthiogalactoside (IPTG) and kept in the same conditions for further 6 hours. The cells collected by centrifugation were resuspended in an equal volume of buffer 0.1M sodium acetate, pH 5.8 and sonicated in a B. BRAUN, model LABSONIC 2000 apparatus for five cycles of 30 seconds each with 1 min intervals on ice. The production of the recombinant enzyme was determined immunologically in the cellular crude, representing approximately the 5% of total soluble proteins. The recombinant fructosyltransferase expressed in E. coli displayed the same catalytic properties as the natural enzyme.

Example 8

Production of an enzymatic preparation with fructosyltransferase activity in recombinant yeast Pichia pastoris.

In order to obtain extracellular expression of the recombinant fructosyltransferase in the methylotrophic yeast Pichia pastoris, the following experiments were performed.

Two oligonucleotides were synthesized: 5'-CATGGCGGCCCGCTCTTCCCC-3' (Seq. Id. No.4) and 5'-GGGGAAGAGCGGGCCGC-3' (Seq. Id. No.5) and hybridized to each other, resulting in a double stranded DNA fragment with one extremity compatible with the NcoI recognition site and one blunt-ended extremity. The sequence of the oligonucleotides was chosen such that the fragment coded for the first six amino acids of the N-terminal region of the mature fructosyltransferase. This synthetic fragment was blunt ligated to the 2.0-kb SmaI fragment of the plasmid pUCLS23 obtaining a NcoI fragment with the entire coding sequence of the mature enzyme, which was then inserted into the cleaved NcoI site of the integrative vector pPS7 (European patent application EP 438 200 A1) resulting in an "in frame" fusion of the Saccharomyces cerevisiae Suc2 signal peptide coding sequence and the fructosyltransferase gene under the control of the alcohol oxidase 1 (AOX1) methanol inducible promoter. This construction named pPSLS20 was PvuII digested and used to transform the Pichia pastoris mutant strain MP36 (his3⁻) (European patent application EP 438 200 A1) according to the procedure described by Meilhoc et al. (Meilhoc et al. (1990), Bio/Technology 8: 223–227). The transformed cells were selected on minimal medium G (P. Galzy, 1957, Paris. C. R. Acad. Sci. 245: 2423–2427) with 2% glucose as carbon source and immunologically screened for fructosyltransferase production. A recombinant yeast expressing high levels of fructosyltransferase after induction with methanol was named strain Lev2.

The production of recombinant fructosyltransferase by Pichia pastoris strain Lev2 was studied in a 5 L fermenter (3.5 L working volume) B. E Marubishi (Tokyo, Japan) in YPG medium (1% yeast extract 1%, peptone 2%, glucose 2%), inoculated at an initial $OD_{530}$ of 0.2, pH 5.2, temperature 30° C., aeration 1 VVM (1 volume per minute), stirring speed 350 rpm. At an optical density of 60 a gradually increasing flow of methanol was fed reaching 3.5 g/h/L, stirring speed was increased from 350 to 750 rpm. The culture was induced during 120 hours.

The enzymatic activity in the culture supernatant increased during induction reaching 5000 U/mL (2 g/L). Following cell disruption with glass beads (Maniatis et al (1989) Molecular Cloning, CSH, NY, USA) it was determined that approximately 25% of the total enzyme produced was secreted to the culture medium.

We claim:

1. A proteinaceous substance having fructosyltransferase activity which comprises a polypeptide having an amino acid sequence as shown in Seq. Id No. 2.

2. A proteinaceous substance having fructosyltransferase activity according to claim 1 which has a molecular weight of about 60000 daltons and an isoelectric point of about 5.5, is stable in a pH range between 4 and 9 and in a temperature range between 10° and 70° C., is active in the presence of 2% SDS, has an activity recovered after 5M urea treatments, has a specific activity of 2600 U/mg, has a Km for sucrose hydrolysis at 30° C. and pH 5.8 of about 12 mM, is not able to transfer fructosyl moieties to inulin and has a low levanase activity.

3. A method for producing a proteinaceous substance having the amino acid sequence shown in Seq. ID No.: 2, which has fructosyltransferase activity, comprising culturing a strain of *Acetobacter diazotrophicus* and recovering the fructosyltransferase enzyme produced.

4. A method according to claim 3 wherein *Acetobacter diazotrophicus* strain SRT4 (CBS 549.94) is used.

5. A method according to claim 3 wherein the fructosyltransferase enzyme produced is recovered from the culture medium.

6. A method for producing fructooligo-saccharides and/or fructans by means of sucrose transfructosylation comprising contacting sucrose under suitable transfructosylation conditions with a fructosyltransferase enzyme and optionally recovering the fructooligosaccharides produced, wherein said fructosyltransferase enzyme is a proteinaceous substance selected from the group consisting of said proteinaceous substance according to claim 1, said proteinaceous substance according to claim 2, and said proteinaceous substance produced according to the method of claim 3.

\* \* \* \* \*

UNITED STATES PATENT AND TRADEMARK OFFICE
CERTIFICATE OF CORRECTION

PATENT NO. : 5,731,173
DATED : March 24, 1998
INVENTOR(S) : Sosa, et al

It is certified that error appears in the above-indentified patent and that said Letters Patent is hereby corrected as shown below:

| | |
|---|---|
| Column 1, Line 6 | now reads "U.S. Pat. No. 5,644,667", should read --U.S. Pat. No. 5,641,667--. |
| Column 1, Line 66, | now reads "1994) and planes (Ebskamp", should read --1994) and plants (Ebskamp--. |
| Column 5, Line 9 | now reads "543.94) is used.," should read -- 549.94) is used.-- |
| Column 6, Line 6 | now reads "low homology wink known", -- should read -- low homology with known--. |
| Column 7, Line 42 | now reads "Sephacryl S-500 column", should read -- Sephacryl 5-500 column--. |
| Column 10, Line 39 | now reads "2.3 kb BglII fragment.," should read -- 2.3 kb BgIII fragment. --. |

UNITED STATES PATENT AND TRADEMARK OFFICE
CERTIFICATE OF CORRECTION

PATENT NO. : 5,731,173
DATED : March 24, 1998
INVENTOR(S) : Sosa, et al

It is certified that error appears in the above-indentified patent and that said Letters Patent is hereby corrected as shown below:

Column 12, Line 38  now reads "approximately 25% of the", should read
-- approximately 85% of the --.

Signed and Sealed this

Twenty-first Day of July, 1998

*Attest:*

*Attesting Officer*

BRUCE LEHMAN

*Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 1632 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO: 1:

```
ATGGCGCACC  GTCCGGGTGT  GATGCCTCGT  GGCGGCCCGC  TCTTCCCCGG  GCGGTCGCTG    60

GCCGGGGTGC  CGGGCTTCCC  GCTGCCCAGC  ATTCATACGC  AGCAGGCGTA  TGACCCGCAG   120

TCGGACTTTA  CCGCCCGCTG  GACACGTGCC  GACGCATTGC  AGATCAAGGC  GCATTCGGAT   180

GCGACGGTCG  CGGCCGGGCA  GAATTCCCTG  CCGGCGCAAC  TGACCATGCC  GAACATCCCG   240

GCGGACTTCC  CGGTGATCAA  TCCGGATGTC  TGGGTCTGGG  ATACCTGGAC  CCTGATCGAC   300
```

-continued

```
AAGCACGCCG ATCAGTTCAG CTATAACGGC TGGGAAGTCA TTTTCTGCCT GACGGCCGAC    360
CCCAATGCCG GATACGGTTT CGACGACCGC CACGTGCATG CCCGCATCGG CTTCTTCTAT    420
CGTCGCGCGG GTATTCCCGC CAGCCGGCGG CCGGTGAATG GCGGCTGGAC CTATGGCGGC    480
CATCTCTTCC CCGACGGAGC CAGCGCGCAG GTCTACGCCG GCCAGACCTA CACGAACCAG    540
GCGGAATGGT CCGGTTCGTC GCGTCTGATG CAGATACATG GCAATACCGT ATCGGTCTTC    600
TATACCGACG TGGCGTTCAA CCGTGACGCC AACGCCAACA ACATCACCCC GCCGCAGGCC    660
ATCATCACCC AGACCCTGGG GCGGATCCAC GCCGACTTCA ACCATGTCTG GTTCACGGGC    720
TTCACCGCCC ACACGCCGCT GCTGCAGCCC GACGGCGTGC TGTATCAGAA CGGTGCGCAG    780
AACGAATTCT TCAATTTCCG CGATCCGTTC ACCTTCGAGG ACCCGAAGCA TCCCGGCGTG    840
AACTACATGG TGTTCGAGGG CAATACCGCG GGCCAGCGTG GCGTCGCCAA CTGCACCGAG    900
GCCGATCTGG GCTTCCGCCC GAACGATCCC AATGCGGAAA CCCTGCAGGA AGTCCTGGAT    960
AGCGGGGCCT ATTACCAGAA GGCCAATATC GGCCTGGCCA TCGCCACGGA TTCGACCCTG   1020
TCGAAATGGA AGTTCCTGTC GCCGCTGATT TCGGCCAACT GCGTCAATGA CCAGACCGAA   1080
CGGCCGCAGG TGTACCTCCA TAACGGAAAA TACTATATCT TCACCATCAG CCACCGCACG   1140
ACCTTCGCGG CCGGTGTCGA TGGACCGGAC GGCGTCTACG GCTTCGTGGG TGACGGCATC   1200
CGCAGTGACT TCCAGCCGAT GAACTATGGC AGCGGCCTGA CGATGGGCAA TCCGACCGAC   1260
CTCAACACGG CGGCAGGCAC GGATTTCGAT CCCAGCCCGG ACCAGAACCC GCGGGCCTTC   1320
CAGTCCTATT CGCACTACGT CATGCCGGGG GGACTGGTTG AATCGTTCAT CGACACGGTG   1380
GAAAACCGTC GCGGGGGTAC CCTGGCGCCC ACGGTCCGGG TGCGCATCGC CCAGAACGCG   1440
TCCGCGGTCG ACCTGCGGTA CGGCAATGGC GGCCTGGGCG CTATGGCGA TATTCCGGCC    1500
AACCGCGCGG ACGTGAACAT CGCCGGCTTC ATCCAGGATC TGTTCGGCCA GCCCACGTCG   1560
GGTCTGGCGG CGCAGGCGTC CACCAACAAT GCCCAGGTGC TGGCGCAGGT TCGCCAATTC   1620
CTGAACCAGT AA                                                      1632
```

(2) INFORMATION FOR SEQ ID NO: 2:

(i) SEQUENCE CHARACTERISTICS:
    (A) LENGTH: 543 amino acids
    (B) TYPE: amino acid
    (C) STRANDEDNESS: unknown
    (D) TOPOLOGY: linear (ii) MOLECULE TYPE: protein (iii) HYPOTHETICAL: NO (xi) SEQUENCE DESCRIPTION: SEQ ID NO: 2:

```
Met Ala His Arg Pro Gly Val Met Pro Arg Gly Gly Pro Leu Phe Pro
 1               5                  10                  15

Gly Arg Ser Leu Ala Gly Val Pro Gly Phe Pro Leu Pro Ser Ile His
            20                  25                  30

Thr Gln Gln Ala Tyr Asp Pro Gln Ser Asp Phe Thr Ala Arg Trp Thr
        35                  40                  45

Arg Ala Asp Ala Leu Gln Ile Lys Ala His Ser Asp Ala Thr Val Ala
    50                  55                  60

Ala Gly Gln Asn Ser Leu Pro Ala Gln Leu Thr Met Pro Asn Ile Pro
65                  70                  75                  80

Ala Asp Phe Pro Val Ile Asn Pro Asp Val Trp Val Trp Asp Thr Trp
                85                  90                  95
```

```
Thr  Leu  Ile  Asp  Lys  His  Ala  Asp  Gln  Phe  Ser  Tyr  Asn  Gly  Trp  Glu
               100                 105                      110

Val  Ile  Phe  Cys  Leu  Thr  Ala  Asp  Pro  Asn  Ala  Gly  Tyr  Gly  Phe  Asp
               115                 120                      125

Asp  Arg  His  Val  His  Ala  Arg  Ile  Gly  Phe  Phe  Tyr  Arg  Arg  Ala  Gly
          130                 135                      140

Ile  Pro  Ala  Ser  Arg  Arg  Pro  Val  Asn  Gly  Trp  Thr  Tyr  Gly  Gly
145                      150                 155                           160

His  Leu  Phe  Pro  Asp  Gly  Ala  Ser  Ala  Gln  Val  Tyr  Ala  Gly  Gln  Thr
                    165                 170                      175

Tyr  Thr  Asn  Gln  Ala  Glu  Trp  Ser  Gly  Ser  Ser  Arg  Leu  Met  Gln  Ile
               180                 185                      190

His  Gly  Asn  Thr  Val  Ser  Val  Phe  Tyr  Thr  Asp  Val  Ala  Phe  Asn  Arg
               195                 200                      205

Asp  Ala  Asn  Ala  Asn  Asn  Ile  Thr  Pro  Pro  Gln  Ala  Ile  Ile  Thr  Gln
          210                 215                      220

Thr  Leu  Gly  Arg  Ile  His  Ala  Asp  Phe  Asn  His  Val  Trp  Phe  Thr  Gly
225                      230                 235                           240

Phe  Thr  Ala  His  Thr  Pro  Leu  Leu  Gln  Pro  Asp  Gly  Val  Leu  Tyr  Gln
                    245                 250                      255

Asn  Gly  Ala  Gln  Asn  Glu  Phe  Phe  Asn  Phe  Arg  Asp  Pro  Phe  Thr  Phe
               260                 265                      270

Glu  Asp  Pro  Lys  His  Pro  Gly  Val  Asn  Tyr  Met  Val  Phe  Glu  Gly  Asn
          275                 280                      285

Thr  Ala  Gly  Gln  Arg  Gly  Val  Ala  Asn  Cys  Thr  Glu  Ala  Asp  Leu  Gly
     290                 295                      300

Phe  Arg  Pro  Asn  Asp  Pro  Asn  Ala  Glu  Thr  Leu  Gln  Glu  Val  Leu  Asp
305                      310                 315                           320

Ser  Gly  Ala  Tyr  Tyr  Gln  Lys  Ala  Asn  Ile  Gly  Leu  Ala  Ile  Ala  Thr
                    325                 330                      335

Asp  Ser  Thr  Leu  Ser  Lys  Trp  Lys  Phe  Leu  Ser  Pro  Leu  Ile  Ser  Ala
               340                 345                      350

Asn  Cys  Val  Asn  Asp  Gln  Thr  Glu  Arg  Pro  Gln  Val  Tyr  Leu  His  Asn
          355                 360                      365

Gly  Lys  Tyr  Tyr  Ile  Phe  Thr  Ile  Ser  His  Arg  Thr  Thr  Phe  Ala  Ala
370                      375                      380

Gly  Val  Asp  Gly  Pro  Asp  Gly  Val  Tyr  Gly  Phe  Val  Gly  Asp  Gly  Ile
385                      390                 395                           400

Arg  Ser  Asp  Phe  Gln  Pro  Met  Asn  Tyr  Gly  Ser  Gly  Leu  Thr  Met  Gly
                    405                 410                      415

Asn  Pro  Thr  Asp  Leu  Asn  Thr  Ala  Ala  Gly  Thr  Asp  Phe  Asp  Pro  Ser
               420                 425                      430

Pro  Asp  Gln  Asn  Pro  Arg  Ala  Phe  Gln  Ser  Tyr  Ser  His  Tyr  Val  Met
          435                 440                      445

Pro  Gly  Gly  Leu  Val  Glu  Ser  Phe  Ile  Asp  Thr  Val  Glu  Asn  Arg  Arg
     450                 455                      460

Gly  Gly  Thr  Leu  Ala  Pro  Thr  Val  Arg  Val  Arg  Ile  Ala  Gln  Asn  Ala
465                      470                 475                           480

Ser  Ala  Val  Asp  Leu  Arg  Tyr  Gly  Asn  Gly  Gly  Leu  Gly  Gly  Tyr  Gly
                    485                 490                      495

Asp  Ile  Pro  Ala  Asn  Arg  Ala  Asp  Val  Asn  Ile  Ala  Gly  Phe  Ile  Gln
               500                 505                      510

Asp  Leu  Phe  Gly  Gln  Pro  Thr  Ser  Gly  Leu  Ala  Ala  Gln  Ala  Ser  Thr
          515                 520                      525
```

```
        Asn  Asn  Ala  Gln  Val  Leu  Ala  Gln  Val  Arg  Gln  Phe  Leu  Asn  Gln
                  530                      535                      540
```

( 2 ) INFORMATION FOR SEQ ID NO: 3:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( x i ) SEQUENCE DESCRIPTION: SEQ ID NO: 3:

```
        Gly  Gly  Pro  Leu  Phe  Pro  Gly  Arg  Ser  Leu
        1                   5                        10
```

( 2 ) INFORMATION FOR SEQ ID NO: 4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO: 4:

```
CATGGCGGCC CGCTCTTCCC C                                              21
```

( 2 ) INFORMATION FOR SEQ ID NO: 5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO: 5:

```
GGGGAAGAGC GGGCCGC                                                   17
```